US00PP31928P2

(12) United States Plant Patent
Holtmaat

(10) Patent No.: US PP31,928 P2
(45) Date of Patent: Jun. 30, 2020

(54) *ECHINACEA* PLANT NAMED 'PARROT'

(50) Latin Name: ***Echinacea* hybrid**
Varietal Denomination: Parrot

(71) Applicant: AB-Kwekersrechten BV, Zuidwolde (NL)

(72) Inventor: Henricus Maria Joseph Holtmaat, Zuidwolde (NL)

(73) Assignee: AB-KWEKERSRECHTEN, BV, Zuidwolde (NL)

( * ) Notice: Subject to any disclaimer, the term of this patent is extended or adjusted under 35 U.S.C. 154(b) by 0 days.

(21) Appl. No.: 16/501,667

(22) Filed: May 20, 2019

(30) Foreign Application Priority Data

Mar. 13, 2019 (QZ) ..... PBR 2019/0679

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ..... A01H 5/02; A01H 6/14
See application file for complete search history.

*Primary Examiner* — Annette H Para
(74) *Attorney, Agent, or Firm* — Penny J. Aguirre

(57) ABSTRACT

A new cultivar of hybrid *Echinacea* plant named 'Parrot' that is characterized by its inflorescences with ray florets that are deep yellow to light yellow in color with red bases, its strong flowering stems, and its short plant height.

2 Drawing Sheets

Botanical classification: *Echinacea* hybrid.
Variety denomination: 'Parrot'.

BACKGROUND OF THE INVENTION

The present invention relates to a new and distinct cultivar of *Echinacea* of hybrid origin and will be referred to hereafter by its cultivar name 'Parrot'. 'Parrot' is an herbaceous perennial grown for landscape and container use.

The new invention arose from an ongoing controlled breeding program in Zuidwolde, The Netherlands. The objective of the breeding program is to develop cultivars of *Echinacea* with unique flowers, strong plant vigor, and short plant habits.

The Inventor discovered the new cultivar as a chance seedling in July of 2017 in a trial field that was planted with seeds collected from numerous cultivars and proprietary plants. The parent plants are therefore unknown.

Asexual propagation of the new cultivar was first accomplished under the direction of the Inventor by tissue culture using meristem tissue in March 2018 in Heerhugowaard, The Netherlands. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Parrot' as unique cultivar of *Echinacea*.

1. 'Parrot' exhibits inflorescences with ray florets that are deep yellow to light yellow in color with red bases.
2. 'Parrot' exhibits strong flowering stems.
3. 'Parrot' exhibits a short plant height.

'Parrot' can be most closely compared to the *Echinacea* cultivars 'Rainb299' (U. S. Plant Pat. No. 28,573) and 'Cleopatra' (U.S. Plant Pat. No. 24,631). 'Rainb299' is similar to 'Parrot' in having a short plant height and in having inflorescences with bi-colored ray florets. 'Cleopatra' differs from 'Parrot' in having stem that are not as strong, in commencing bloom earlier in the season, and in having inflorescences with ray florets that are yellow in color and not bi-colored.

BRIEF DESCRIPTION OF THE DRAWINGS

The accompanying colored photographs illustrate the overall appearance and distinct characteristics of the new *Echinacea*. The photographs were taken of a ten-month-old plant of the new cultivar grown outdoors in a 13-cm container in Zuidwolde, The Netherlands.

The photograph in FIG. 1 illustrates the overall habit and appearance of 'Parrot' in bloom.

Figure 1:
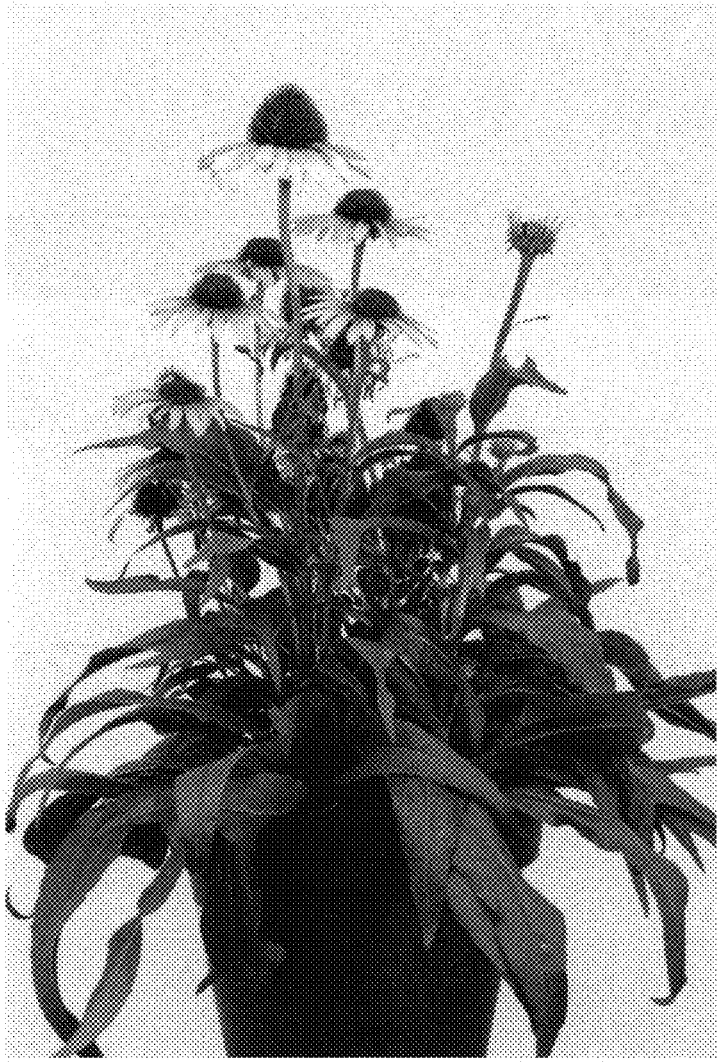
Figure 2:
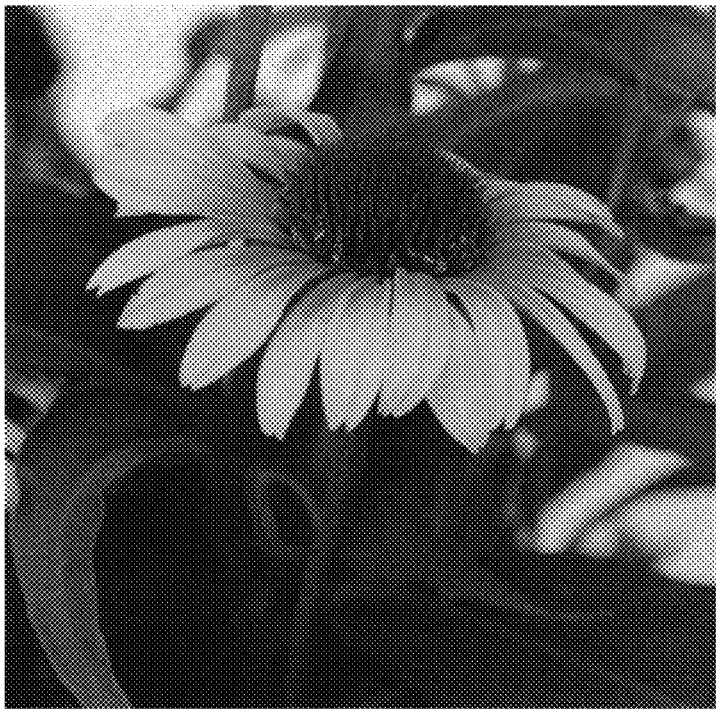

The photograph in FIG. 2 provides a close-up view of the inflorescences of 'Parrot'.

Figure 3:
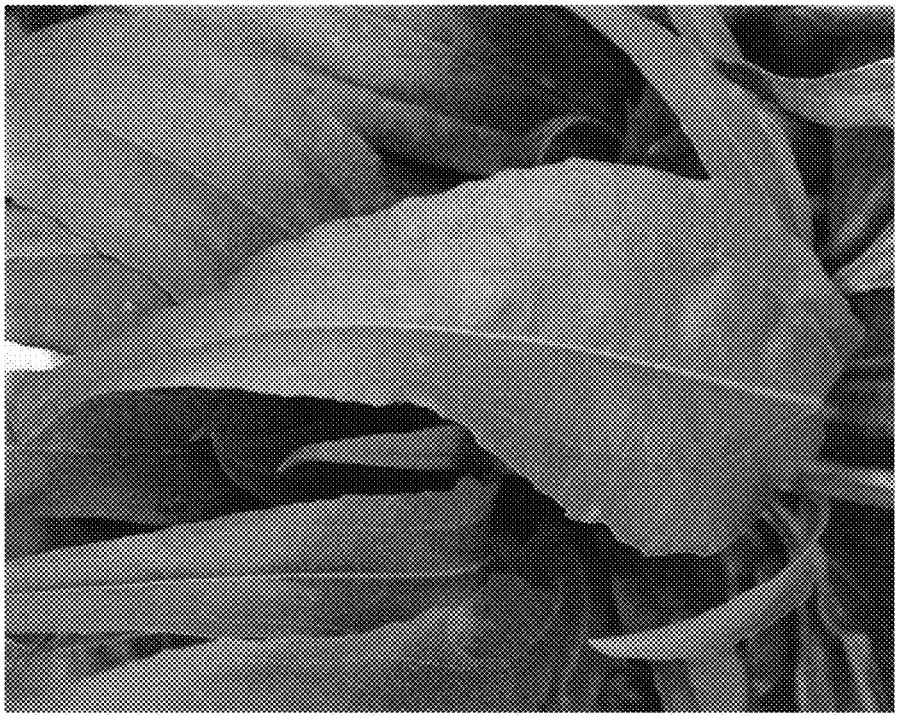

The photograph in FIG. 3 provides a close-up view of a leaf of 'Parrot'.

The colors in the photographs are as close as possible with the photographic and printing technology utilized and color values cited in the detailed botanical description accurately describe the colors of the new *Echinacea*.

DETAILED BOTANICAL DESCRIPTION

The following is a detailed description of ten-month-old plants of the new cultivar as grown outdoors in a 13-cm container in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms for 10 weeks from July to late September, in The Netherlands.

*Plant type*.—Herbaceous perennial.

*Plant habit*.—Compact, short, broad ovate in shape, upright.

*Height and spread*.—An average of 55 cm in height and 50 cm in spread when grown outdoors.

*Hardiness*.—At least to U.S.D.A Zones 4 to 9.

*Disease and pest resistance*.—No susceptibility and resistance to diseases and pests has been observed.

*Root description*.—Fibrous and fine, 158D in color.

*Propagation*.—Tissue culture using meristem tissue and division.

*Growth rate*.—Moderate.

*Root development*.—Rooting occurs in about 10 weeks and a young rooted plant can be produced in about 3 months.

Stem description:

*Shape*.—Rounded.

*Stem color*.—144B and moderately flushed and dotted with N186C.

*Stem size*.—An average of 30 cm in length and 7 mm in diameter.

*Stem strength*.—Very strong.

*Stem aspect*.—Grows at an average angle of 22.5° from the base (0°=vertical).

*Stem surface*.—Glabrous.

*Stem number*.—Average of 5 main branches.

*Internode length*.—Average of 3.2 cm in length.

*Branching*.—Main flowering stem grows from base.

Foliage description:

*Leaf shape*.—Basal and cauline leaves moderately carinate, basal leaves ovate to narrow ovate, cauline leaves ovate to narrow ovate.

*Leaf division*.—Simple.

*Leaf base*.—Basal leaves and cauline leaves attenuate.

*Leaf apex*.—Basal leaves acute and cauline leaves narrow acute to narrow acute.

*Leaf venation*.—Pinnate, basal and cauline leaves; 146C in color on upper surface and 144B in color on lower surface.

*Leaf margins*.—Basal leaves and cauline leaves entire and slightly to moderately undulate.

*Leaf attachment*.—Petiolate.

*Leaf arrangement*.—Alternate.

*Leaf size*.—Basal leaves average of 26.7 cm in length and 5.8 cm in width, cauline leaves average of 19.4 cm in length and 5.0 cm in width.

*Leaf color*.—Basal and cauline leaves: young upper surface; slightly darker than 137B, young lower surface; 138A, mature upper surface; NN137A, mature lower surface; 137B.

*Leaf surface*.—Basal and cauline leaves; upper surface very slightly glossy, rough to touch, moderately covered with very short strigose hairs; an average of 0.4 mm in length and too fine to measure color, lower surface matte and rough to touch.

*Petioles*.—V-shaped, strong, basal leaves an average of 13.4 cm in length and 3 mm in diameter, cauline leaves an average of 5.2 cm in length and 3 mm in diameter, color upper surface 144B with 184A towards the proximal end, margin NN137B, color lower surface 144A, both surfaces smooth and glabrous.

Flower description:

*Type*.—Terminal capitulums consisting of ray florets and disc florets.

*Capitulum number*.—An average of 6 per stem, 24 per plant.

*Lastingness of inflorescence*.—A few weeks, ray florets self-cleaning.

*Capitulum size*.—Matures to about 3.7 cm in height and 8.5 cm in diameter, disc diameter is an average of 4.4 cm.

*Inflorescence aspect*.—Held straight on top of peduncles.

*Fragrance*.—Faint, sweet and somewhat cinnamon-like.

*Involucral bracts or phyllary*.—Rotate spirally 60 arranged in 3 overlapping rows, average of 8 mm in length and 3 mm in width, cuneate base, acute apex, ovate to narrow ovate in shape, margins entire, color upper and lower surface 143A, upper surface texture; smooth, lower surface and margin texture; moderately covered with very short strigose hairs; an average of 0.3 mm in length and too fine for color reading.

*Inflorescence buds*.—Flattened globular in shape, immature ray florets pointed upward (near vertical), an average of 2.8 cm in length and 3.7 cm in diameter, color 175A with immature ray florets 151D, matte surface texture.

*Peduncle*.—Strong, terminal and secondary an average of 13.3 cm in length (from uppermost leaf to base of inflorescence) and 3.5 mm in diameter, aspect of terminal straight on top of main (flowering) stem, average angle of secondary peduncles: 25° (0°=straight upright), 145A in color and moderately flushed and dotted with 197A and 197B, surface is slightly glossy, very sparsely covered with very short strigose hairs an average of 0.4 mm in length, color too small and too sparsely present to be measured with color chart.

*Ray florets*.—Rotate around disc in 1 row, average of 25 (varying between 20 and 35) per inflorescence, narrow elliptic to near narrow oblong in shape, average of 4.1 cm in length and 0.9 cm in width, emarginate to praemorse apex, cuneate base, entire margin, held at an average angle of −30° downward to horizontal, color; upper surface when opening 16A, lower ⅖th of ray floret 42B, lower surface when opening 11C, margins 31D and changing towards the base to 41D, upper surface when fully open 14C, lower ⅖th of ray floret 45C, lower surface when fully open 11C and fading changing towards the base to 41D, when fading upper surface; 11C and strongly tinged towards base with 51C, when fading lower surface; 11D with margins tinted 51D, surface texture; upper surface glabrous, matte and carinate, lower surface glabrous, slightly glossy and carinate.

*Disk flowers* (*bisexual*).—Numerous, average of 260, arranged spirally on disc, tubular, upright to outward aspect, apex is acute on upper 15% that is free, fused (tubular) base, entire margin, average of 1.15 cm in length and 2 nun in width, upper and lower surface textures are smooth, glabrous and glossy, color when opening upper and lower surface; apex 181B mid-section and base 146D, color when fully open upper and lower surface; apex 144B mid-section and base 145C.

*Disk spines*.—Average of 260, acicular in shape, acute apex, attenuate base, glabrous and glossy surface, color is 202A, 46A and 23B at apex, 143A in mid region and 145D at base.

*Receptacle*.—Ovate in shape, an average of 9 mm in height and 7 mm in diameter, and NN155B in color.

Reproductive organs (present on disk florets only):

*Gynoecium*.—Pistil; average 1; 8 mm in length, style; 6 mm in length and 185B in color changing towards base to 150D, stigma; unequal decurrent, color in between 187A and 203C, ovary; 145D in color.

*Androcoecium*.—Stamens; 5, filaments; 2 mm in length and 154D in color, anthers; linear in shape, average 3 mm in length, 200A in color, pollen is moderate in quantity and 17A in color.

*Fruit/seed*.—No seed production has been observed.

It is claimed:

1. A new and distinct cultivar of *Echinacea* plant named 'Parrot' as herein illustrated and described.

* * * * *